United States Patent [19]

Jenkins

[11] Patent Number: 4,796,284
[45] Date of Patent: Jan. 3, 1989

[54] POLYCRYSTALLINE X-RAY SPECTROMETER

[75] Inventor: Ronald Jenkins, Downingtown, Pa.

[73] Assignee: North American Philips Corporation, New York, N.Y.

[21] Appl. No.: 929,960

[22] Filed: Nov. 10, 1986

Related U.S. Application Data

[63] Continuation-in-part of Ser. No. 688,096, Dec. 31, 1984, abandoned.

[51] Int. Cl.⁴ .................... G01N 23/20; G01N 23/22
[52] U.S. Cl. .................................... 378/49; 378/45; 378/75; 378/85; 378/83
[58] Field of Search ............... 378/49, 46, 45, 44, 378/85, 84, 83, 82, 75, 71, 70

[56] References Cited

U.S. PATENT DOCUMENTS

| | | | |
|---|---|---|---|
| 3,424,428 | 1/1969 | Canon | 378/49 |
| 3,806,726 | 4/1974 | Ishijima | 378/49 |
| 4,472,825 | 9/1984 | Jenkins | 378/85 |

FOREIGN PATENT DOCUMENTS 203394  10/1983  German Democratic Rep. ... 378/71

OTHER PUBLICATIONS

Jenkins, R., "Combination of the Energy Dispersion Spectrometer with the Powder Diffractometer," Norelco Reporter, vol. 20, No. 3, Dec. 1973, pp. 22-30.

Primary Examiner—Craig E. Church
Assistant Examiner—T. N. Grigsby
Attorney, Agent, or Firm—Paul R. Miller

[57] ABSTRACT

A wavelength dispersive X-ray spectrometer is provided with a polycrystalline analyzer for analyzing characteristic spectra of a sample. The polycrystalline analyzer provides a multiple spectrum of characteristic lines which are separated by appropriate pulse height analysis. Each of these sets of characteristic lines of the elements of the sample are provided at different dispersion and wavelength ranges.

2 Claims, 2 Drawing Sheets

POLYCRYSTALLINE X-RAY SPECTROMETER

This is a continuation-in-part of previous application Ser. No. 688,096, filed Dec. 31, 1984, now abandoned, and priority for all common subject matter is hereby claimed.

The present invention is directed to a wavelength dispersive X-ray spectrometer allowing the separation in $\theta$ space of intensities from a polychromatic beam of radiation excited from a sample consisting of many elements, wherein the individual intensities and therefore the individual elements can be measured. More particularly, the wavelength dispersive spectrometer utilizes a polycrystalline analyzing crystal for measuring the broad spectrum of $\theta$ angles.

Wavelength dispersive spectrometers are commercially available in a broad range of devices. Primarily, such X-ray spectrometers are equipped with 3 to 6 analyzing crystals to allow a broad wavelength range to be measured. In particular, a wavelength range of from about 0.2 to 20 Angstroms can be measured.

In prior X-ray spectrometers, a number of single crystal analyzers have to be used in order to achieve measurements over a broad wavelength range. Principally, the spacings of individual single crystals were such that only a small part of the wavelength range could be achieved with an individual single crystal in the measurement of the spectrum, while maintaining optimum spectral dispersion. Consequently, a number of analyzing crystals were used with a dispersion in characteristic values in order to achieve measurement over a large wavelength spectrum.

The wavelength dispersive spectrometer provides separation in $\theta$ space of intensities from a polychromatic beam of radiation excited from a sample consisting of many elements. Accordingly, by measurement of individual intensities, the elements an their concentration can be measured. The separation in $\theta$ space is achieved by allowing the beam of radiation from the specimen or sample to fall onto the surface of the single analyzing crystal. This crystal has been cleaved such that certain crystallographic planes are parallel to its surface. The measurable wavelength $\lambda$ is related to the diffraction angle $\theta$ by the expression $$n\lambda = 2d \sin \theta \quad (1)$$

where n is an integer and d is the interplanar spacing of the single crystal used for diffraction. The separation of lines in the spectrum is a function mainly of the d spacing of the crystal, and in fact, the angular separation $d\theta$ of two wavelengths, $\lambda_1$ and $\lambda_2$, of a wavelength difference $d\lambda$, is given by $$d\theta/d\lambda = n/(2d \cos \theta) \quad (2).$$

Because of instrumental constraints, the range of $\theta$ is limited to be between 5° and 75°. Accordingly, a large value of d, the interplanar spacing, must be selected for the measurement of a long wavelength, whereas the separation of lines improves with a decrease of d values. This in turn requires that for the measurement of many wavelengths, i.e. many elements, several crystals must be employed. As noted above, traditional wavelength dispersive X-ray spectrometers are typically supplied with between 3 and 6 analyzing single crystals to allow the measurements to be made over the wavelength range from about 0.2 to 20 Angstroms.

The presently claimed invention seeks to avoid the use of a multiple number of single crystals to obtain the wavelength spectra.

Accordingly, the analyzing crystal according to the present invention is a polycrystalline material and electronic analysis is provided of a spectrum.

The features and advantages of the present invention will be described in more detail, by way of example, with reference to the drawing figures, in which.

Figure 1:
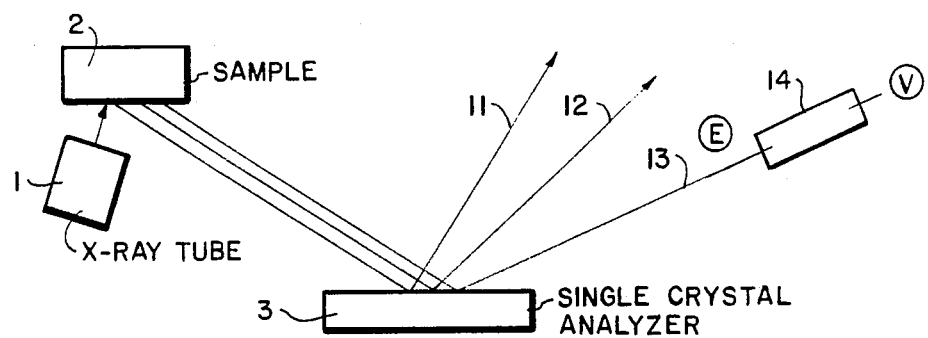
FIG. 1 is an example of the prior art.

A wavelength dispersive spectrometer of the prior art using single crystals for wavelength measurement of a material to determine characteristic elements of the material is seen in FIG. 1. An X-ray tube 1 directs an X-ray beam onto a characteristic sample 2. Each element in the sample emits a characteristic X-ray line series of radiation onto an analyzing crystal 3, which is one of a number of single crystals. Each single crystal disperses radiation from the elements according to the d spacing of that particular single crystal. In the interest of simplicity, only three characteristic lines 11, 12, and 13 are shown in the figure. Each of these characteristic lines represents individual wavelengths to be measured, thereby identifying the material. A detector 14 converts the energy E of each diffracted X-ray photons into a voltage pulse V. The values of E and V are related by the expression $$V = AE \quad (3)$$

where A is a measure of the amplification of the detector circuit.

Figure 2:
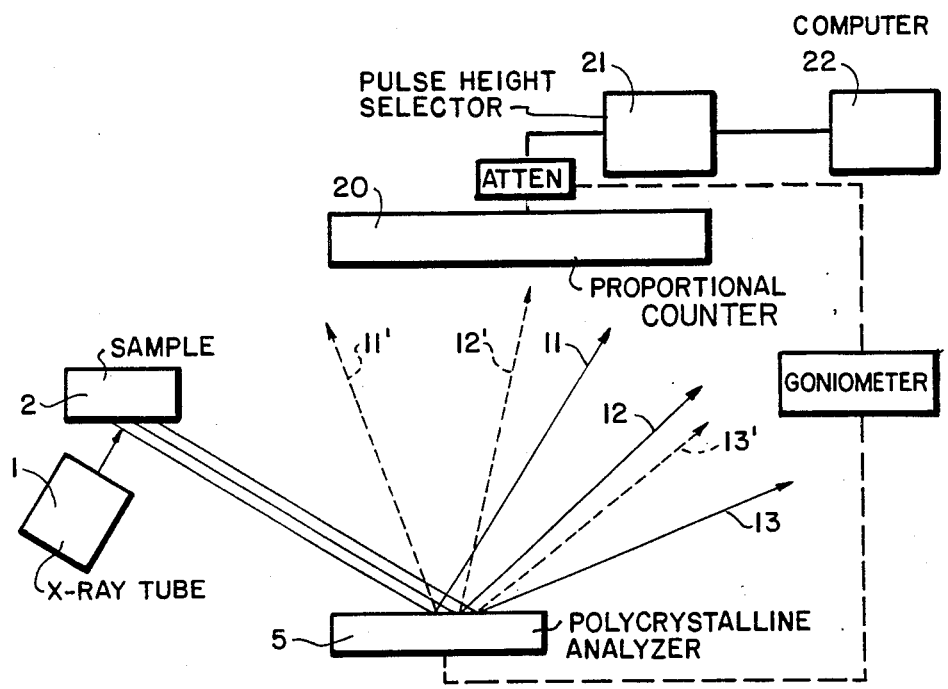
FIG. 2 illustrates the presently claimed invention.

According to the present invention, a polycrystalline analyzing crystal 5 is utilized, as seen in FIG. 2, instead of the single crystal structure of FIG. 1. The polycrystalline arrangement 5 enables each set of planes in the crystal lattice to diffract with the characteristic lines.

The polycrystalline structure 5 can be made by a single crystal of a known crystallographic system which has been ground up and pelletized to the dimensions of an analyzing crystal, or it can be a polycrystalline mixture of two or more materials chosen to give the required characteristics. In either case, the interplanar spacings "d" of the various crystallographic planes are known, and hence, the possible "reflections" from the polycrystal are also known. As an example, lithium fluoride (LiF) was used in one experiment in which the following planes were diffracted within the angular range of the spectrometer: (111)d=1.162; (200)d=1.006; (220)d=0.712; (311)d=0.607; (331)d=0.462; (420)d=0.450; and (422)d=0.411.

FIG. 2 shows, as an example in the interest of simplicity, only two sets of lines. These are illustrated by the two sets of lines 11, 12, and 13, and 11', 12', and 13'. Because the dispersion of the spectrometer is a function of the d spacing causing diffraction, the dispersion of these two sets of lines is different. The result of using the polycrystalline analyzing crystal 5 is to produce multiple sets of line spectra, superimposed on top of each other. Each one of these spectra is characteristic of the elements in the sample, but each one has a different dispersion and wavelength range. Since wavelength λ and photon energy E are inversely related, it can be derived from equations (1) and (3) that the voltage output V from the detector is given by $$V = \frac{n}{2d}\left(\frac{A}{\sin\theta}\right) \qquad (4)$$

Thus, by varying the amplification of the output detector pulses as a function of sin $\theta$, a linear relationship is obtained between the $\theta$ angle and the voltage output. The voltage output is proportional to the energy of the characteristic X-ray photon and inversely proportional to the wavelength. A series of calibration curves can now be readily derived for λ, E or atomic number Z, as a function of diffraction angle with one such curve for each value of d in equation (4). By use of a pulse height selection circuit 20-22, seen in FIG. 2, the spectrometer is first calibrated with a single element standard, for example, iron. This single element standard gives a single calibration point for each of the sets of diffracting planes for the polycrystal in question. From this point on, the calibration is held automatically with angular calibration of the attenuation. Hence, it is possible to tune the scaling and counting electronics such that just one of the spectral series is selected. That is, by utilizing a proportional counter 20 feeding a pulse height selector 21, the different spectral series can be selected. This selection may be further seen by reference to FIGS. 3 and 4. The different spectral series are analyzed in a computer 22.

Figure 3:
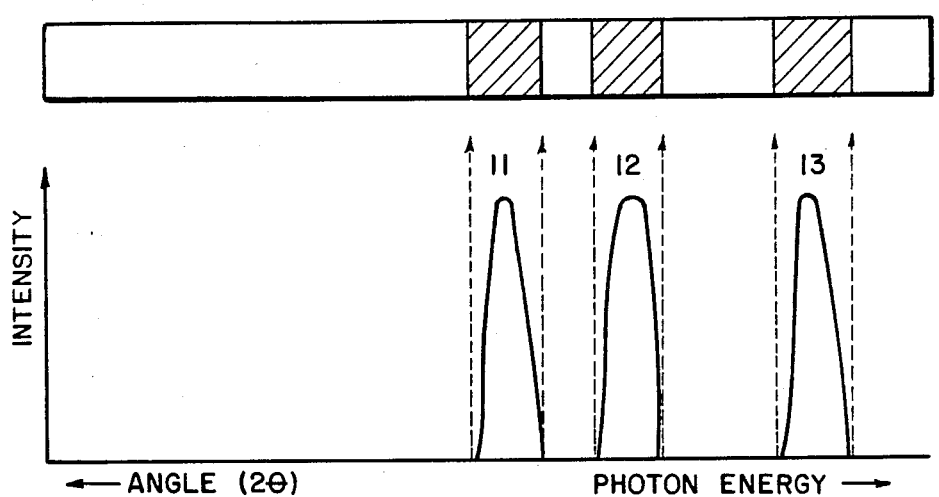
FIG. 3 illustrates the principle used in the prior art of FIG. 1.

FIG. 3 illustrates the principle used in the prior state of the art. Since the analyzing crystal, such as 3 in FIG. 1, is scanned with a goniometer structure through a range of diffraction angles 2$\theta$, an intensity/angle diagram is generated as shown in FIG. 3. Since the diffraction angle is inversely related to the energy of hhe diffracting photons, as the value of 2$\theta$ increases, the energy of the radiation being diffracted decreases. Accordingly, the spectrum can also be considered as an intensity/energy diagram.

A proportional detector, like 20 in FIG. 2, is used to convert the energy of the diffracted X-ray photons to individual voltage pulses with the pulse rate from the proportional detector being a measure of the photon rate entering the detector. In the technique of pulse height selection, a fixed voltage level acceptance window is employed in a pulse height selector, such as 21 in FIG. 2, to reject all extraneous and noise pllses. However, since the magnitude of each output pulse from the detector is proportional to the photon energy, the size of the individual voltage pulses being diffracted also decreases with goniometer angle, and it is necessary to attenuate the voltage pulses leaving the detector so that they will fall within the preselected acceptance window of the pulse height selector. This attenuation is performed using a linear resistor which is coupled to the goniometer on which the analyzing crystal is mounted giving a sinusoidal attenuation factor. The system is calibrated by adjusting the gain of the proportional detector 220 by varying in turn the high voltage on the detector. The acceptance by the pulse height selector 21 is indicated at the top of FIG. 3.

Figure 4:
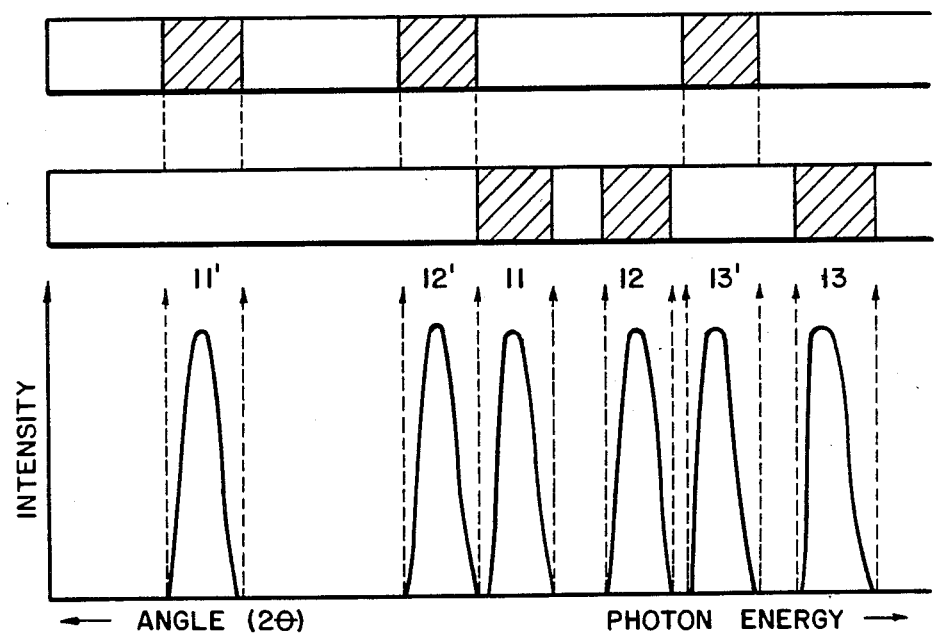
FIG. 4 illustrates the operation of the present invention.

In the present invention, the selection of a given spectral series is made by simply adjusting the gain of the counting system relative to the value obtained from the single element calibration standard. Thus, to accept the series of lines 11, 12 and 13, for example, a first gain setting is chosen. To accept a second series of lines 11', 12' and 13', for example, another gain setting is chosen. These gain settings are typically controlled by a microprocessor, such as 22 in FIG. 2, so that the selection of one line series or another is completely automated. In FIG. 4, the spectrum is shown as it would be acquired according to the present invention. The acceptance by the pulse height selector 21 for the two mentioned different gain settings is shown at the top of the figure.

What is claimed:

1. In an X-ray spectrometer including a source of X-rays, a sample receiving X-rays from said source, said sample emitting characteristic radiation, analyzing means receiving said characteristic radiation for producing reflected radiation, and detector means receiving said reflected radiation for detecting concentrations of said sample, said detector means including proportional detector means for generating voltage pulses is response to said reflected radiation, the improvement comprising said analyzing means including a goniometer and a polycrystalline material disposed on said goniometer, said polycrysatlline material being a pellet of at least one ground-up crystalline material, wherein said detector means include variable attenuating means connected to the output of said proportional detector means for attenuating the intensity of said pulses, said attenuating means being connected to and controlled by said gonimeter such that the amount of attenuation varies with angular displacement of the goniometer.

2. An X-ray spectrometer according to claim 1, wherein said detector means includes a programmable pulse height selector circuit means for providing a plurality of acceptance windows, each acceptance window being sufficiently narrow to select a single series of wavelengths at a time, and wherein said acceptance windows are automatically selected by a microprocessor.

* * * * *